US 12,239,480 B2

(12) United States Patent
Dong et al.

(10) Patent No.: US 12,239,480 B2
(45) Date of Patent: Mar. 4, 2025

(54) ULTRASOUND IMAGING METHODS AND SYSTEMS AND COMPUTER STORAGE MEDIUM

(71) Applicant: SHENZHEN MINDRAY BIO-MEDICAL ELECTRONICS CO., LTD., Guangdong (CN)

(72) Inventors: Yongqiang Dong, Shenzhen (CN); Yan Wang, Shenzhen (CN); Zhiwei Shi, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 93 days.

(21) Appl. No.: 18/082,263

(22) Filed: Dec. 15, 2022

(65) Prior Publication Data

US 2023/0371918 A1 Nov. 23, 2023

Related U.S. Application Data

(63) Continuation of application No. PCT/CN2020/096375, filed on Jun. 16, 2020.

(51) Int. Cl.
*A61B 8/06* (2006.01)
*A61B 8/00* (2006.01)

(52) U.S. Cl.
CPC .............. *A61B 8/06* (2013.01); *A61B 8/5207* (2013.01)

(58) Field of Classification Search
CPC ......... A61B 8/06; A61B 8/488; A61B 8/5207; A61B 8/5223; A61B 8/54; G01S 15/8977; G01S 15/8979
See application file for complete search history.

(56) References Cited

U.S. PATENT DOCUMENTS

| 9,173,640 B2 | 11/2015 | Lin |
| 2006/0122510 A1 | 6/2006 | Miyaki |
| 2019/0320998 A1 | 10/2019 | Yu et al. |

FOREIGN PATENT DOCUMENTS

| CN | 102133089 A | 7/2011 |
| CN | 104490422 A | 4/2015 |
| CN | 108852415 A | 11/2018 |
| CN | 110946617 A | 4/2020 |
| CN | 111265246 A | 6/2020 |

OTHER PUBLICATIONS

PCT International Search Report and the Written Opinion mailed Mar. 16, 2021, issued in related International Application No. PCT/CN2020/096375, with partial English translation (12 pages).

*Primary Examiner* — Mark D Remaly
(74) *Attorney, Agent, or Firm* — Sheppard Mullin Richter & Hampton LLP

(57) ABSTRACT

Disclosed are an ultrasonic imaging method, an ultrasonic imaging system and a computer storage medium. The method includes: transmitting ultrasonic waves to a region of interest, including transmitting multiple pulses to the same target position (S110); receiving ultrasonic echoes to obtain an ultrasonic echo signal (S120); performing beam synthesis to obtain a beam-synthesized signal for each transmission (S130); performing autocorrelation calculation on the beam-synthesized signal for each transmission to obtain an autocorrelation function characterizing the blood flow signal for each transmission (S140); synthesizing the autocorrelation functions obtained after multiple transmissions to obtain a synthesized autocorrelation function (S150); and obtaining a color blood flow image based on the synthesized autocorrelation function (S160).

19 Claims, 7 Drawing Sheets transmitting an ultrasonic wave to a region of interest of a target object and receiving an ultrasonic echo of the ultrasonic wave to obtain an ultrasonic echo signal — S101 processing the ultrasonic echo signal to obtain an autocorrelation function representing a blood flow signal — S102 performing complex coefficient weighting on the autocorrelation function to obtain a synthetic autocorrelation function — S103 obtaining a color blood flow image of the region of interest based on the synthetic autocorrelation function — S104

FIG. 3 transmitting an ultrasonic wave to a region of interest of a target object and receiving an ultrasonic echo of the ultrasonic wave to obtain an ultrasonic echo signal — S210 performing beam synthesis on the ultrasonic echo signal to obtain a beam synthesized signal — S220 processing the beam synthesized signal in autocorrelation domain to obtain an autocorrelation function representing a blood flow signal — S230 processing the autocorrelation function with an operation structure of an optimal filter — S240

FIG. 7

ULTRASOUND IMAGING METHODS AND SYSTEMS AND COMPUTER STORAGE MEDIUM

TECHNICAL FIELD

Embodiments of the present disclosure relates to ultrasound, and more particularly to ultrasound imaging methods, ultrasound imaging systems and computer storage media.

BACKGROUND

Transmission continuous focusing methods may be adopted to combine echo signals of ultrasound waves transmitted multiple times in an effective transmitting region during performing ultrasonic imaging on tissues, improving sensitivity and penetration.

However, it is unsuitable to directly apply the transmission continuous focusing methods to color blood flow imaging due to the motion property of blood flow. It can be seen that for color blood flow imaging, other methods need to be considered in order to improve the lateral resolution of images and enhance the sensitivity of the images and penetration.

SUMMARY

In one embodiment, an ultrasonic imaging method may include:
transmitting ultrasonic waves to a region of interest of a target object, said transmitting ultrasonic waves comprising transmitting pulses to a same target position for multiple times;
receiving ultrasonic echoes of the ultrasonic waves to obtain ultrasonic echo signals;
performing a beam synthesis on the ultrasonic echo signals obtained by each transmission to obtain a beam synthesized signal of each transmission;
performing an autocorrelation calculation on the beam synthesized signal of each transmission to obtain an autocorrelation function of each transmission representing a blood flow signal;
performing a synthesis on the autocorrelation functions of the multiple transmissions to obtain a synthetic autocorrelation function; and
obtaining a color blood flow image of the region of interest according to the synthetic autocorrelation function.

In one embodiment, an ultrasonic imaging method may include:
transmitting an ultrasonic wave to a region of interest of a target object and receiving an ultrasonic echo of the ultrasonic wave to obtain an ultrasonic echo signal;
processing the ultrasonic echo signal to obtain an autocorrelation function representing a blood flow signal;
performing a complex coefficient weighting on the autocorrelation function to obtain a synthetic autocorrelation function; and
obtaining a color blood flow image of the region of interest based on the synthetic autocorrelation function.

In one embodiment, an ultrasonic signal processing method may include:
transmitting an ultrasonic wave to a region of interest of a target object and receiving an ultrasonic echo of the ultrasonic wave to obtain an ultrasonic echo signal;
performing a beam synthesis on the ultrasonic echo signal to obtain a beam synthesized signal;
processing the beam synthesized signal in autocorrelation domain to obtain an autocorrelation function representing a blood flow signal; and
processing the autocorrelation function with an operation structure of an optimal filter.

In one embodiment, an ultrasonic imaging system may include:
an ultrasonic probe;
a transmitting circuit configured to excite the ultrasonic probe to transmit ultrasonic waves to a region of interest of a target object, wherein transmitting the ultrasonic waves comprises transmitting pulses to a same target position for multiple times;
a receiving circuit configured to receive ultrasonic echoes of the ultrasonic waves via the ultrasonic probe to obtain ultrasonic echo signals;
a memory configured to store a program executed by a processor; and
the processor configured to execute the program to:
perform a beam synthesis on the ultrasonic echo signal obtained by each transmission to obtain a beam synthesized signal of each transmission;
perform an autocorrelation calculation on the beam synthesized signal of each transmission to obtain an autocorrelation function representing a blood flow signal of each transmission;
perform a synthesis on the autocorrelation functions of the multiple transmissions to obtain a synthetic autocorrelation function; and
obtain a color blood flow image of the region of interest based on the synthetic autocorrelation function.

In one embodiment, a computer storage medium may be provided, on which a computer program is stored, where the computer program may be executed by a computer or a processor to implement any one of the methods mentioned in the above.

Thus, it can be seen that the embodiment of the present disclosure can realize synthesis based on transmission continuous focusing in autocorrelation domain. Specifically, the synthesis can be carried out after the autocorrelation function is obtained through an autocorrelation calculation, and it can only be processed based on scalar(s), avoiding energy offset caused by opposite phases of signals caused by the flow characteristics of the blood flow and improving the lateral resolution of the color blood flow image, thereby improving the sensitivity and penetration of blood flow image.

BRIEF DESCRIPTION OF THE DRAWINGS

In order to more clearly illustrate the technical solution of the embodiments of the present disclosure, the appended drawings required to be used in the description of the embodiments or the prior art are briefly introduced below. It is obvious that the appended drawings described below are only embodiments of the present disclosure. For those skilled in the art, they may also obtain other drawings based on these drawings without creative labor.

FIG. 3 is a schematic flowchart of an ultrasonic imaging method according to an embodiment of the present disclosure;

FIG. 7 is a schematic flowchart of an ultrasonic signal processing method according to an embodiment of the present disclosure.

DETAILED DESCRIPTION

An ultrasonic imaging system provided in accordance with an embodiment of the present disclosure can be used to obtain color blood flow images.

Figure 1:
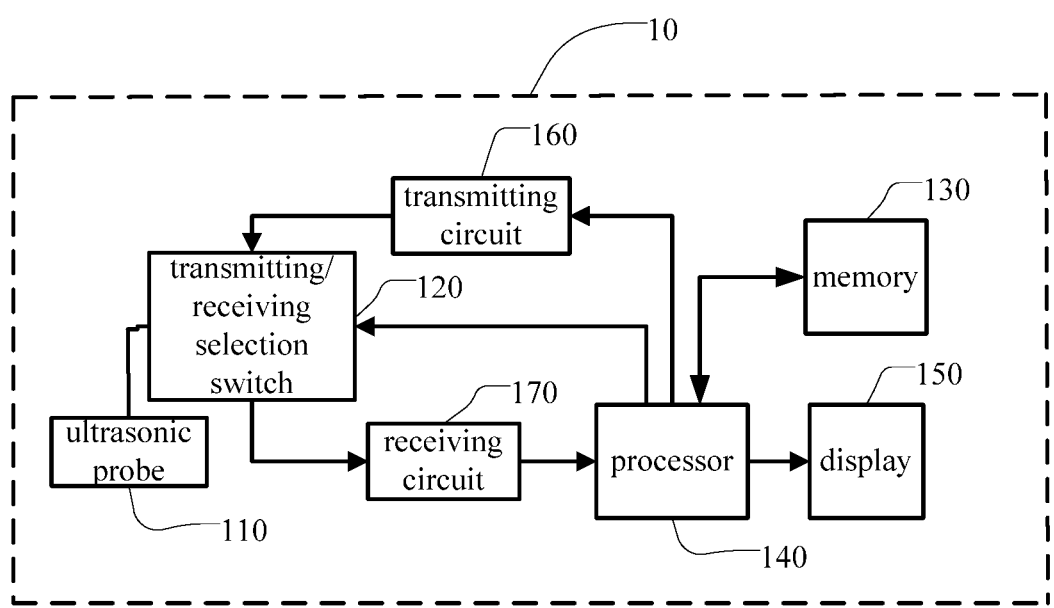
FIG. 1 is a block diagram of an ultrasonic imaging system.

FIG. 1 shows a block diagram of an ultrasonic imaging system. The ultrasonic imaging system 10 may include an ultrasonic probe 110, a transmitting/receiving selection switch 120, a transmitting circuit 160, a receiving circuit 170, a memory 130, a processor 140 and a display 150. The transmitting circuit 160 may transmit exciting pulses to the ultrasonic probe 110 via the transmitting/receiving selection switch 120 to excite the ultrasonic probe 110 to transmit ultrasonic beams to a target object. The receiving circuit 170 may receive an ultrasonic echo of a returned ultrasonic beam via the ultrasonic probe 110 to obtain an ultrasonic echo signal, and send the ultrasonic echo signal to the processor 140. The processor 140 may process the ultrasonic echo signal.

Exemplarily, the ultrasonic probe 110 may be excited to transmit an ultrasonic beam to the region (which may include vessels) of interest of the target object and receive an ultrasonic echo of the ultrasonic beam from the region via the ultrasonic probe 110 to obtain the ultrasonic echo signal. The processor 140 may determine an autocorrelation function representing a blood flow signal based on the ultrasonic echo signal.

The ultrasonic beam transmitted once may include transmitting pulses to a same target position for multiple times. The processor 140 may obtain the autocorrelation function representing a blood flow signal for each pulse; perform synthesis on the autocorrelation function representing a blood flow signal obtained by multiple transmission to obtain a synthetic autocorrelation function; and obtain a color blood flow image based on the synthetic autocorrelation function.

Optionally, the display 150 of the ultrasonic imaging system 10 may be a touch screen, a liquid crystal display, or the like; or, the display 150 may be an independent display device (such as a liquid crystal display, a television, etc.) Independent of the ultrasonic imaging system 10; or, the display 150 may be a display screen of an electronic device (such as a smart phone, a tablet computer, etc.). The number of the display 150 may be one or more.

Optionally, the memory 130 of the ultrasonic imaging system 10 may be a flash memory card, a solid-state memory, a hard disk or the like. It may be volatile memory and/or non-volatile memory, be a removable memory and/or non-removable memory.

Optionally, the processor 140 of the ultrasonic imaging system may be realized by software, hardware, firmware or any combination thereof. The processor may perform corresponding steps of the methods in various embodiments of the present disclosure by using circuit(s), single or multiple application specific integrated circuits (ASICs), single or multiple general integrated circuits, single or multiple microprocessors, single or multiple programmable logic devices, or any combination of the aforesaid circuits and/or devices or other suitable circuits or devices.

It should be understood that the components included in the ultrasonic imaging system 10 shown in FIG. 1 are only schematic and may be more or fewer. For example, the ultrasonic imaging system 10 may further include an input unit such as a keyboard, a mouse, a wheel, a trackball and the like, and/or an output unit such as a printer. A corresponding external input/output port may be a wireless communication unit, or a wired communication unit, or a combination of the two. The external input/output port may also be implemented based on USB, bus protocol(s) such as CAN, and/or wired network protocol(s). The present disclosure is not limited to this.

The transmission continuous focusing methods are mainly used for tissue imaging, which improves sensitivity and penetration because they combine echo signals obtained by multiple transmission in an effective region of transmission. Secondly, the transmission continuous focusing methods can expand the transmitting aperture to improve the lateral resolution of the image because of combination of multiple transmission.

It is also a requirement for color blood flow imaging to improve the lateral resolution of image(s) together with the sensitivity and penetration of image(s), however, because of some technical differences between color blood flow imaging and tissue imaging, the transmission continuous focusing methods cannot be directly used in color blood flow imaging.

The transmission scanning mechanisms of color blood flow imaging and tissue imaging are different. As shown in FIG. 2, different line widths may represent different transmission, wherein the downward arrow represents transmission and the upward arrow represents reception.

Figure 2B:
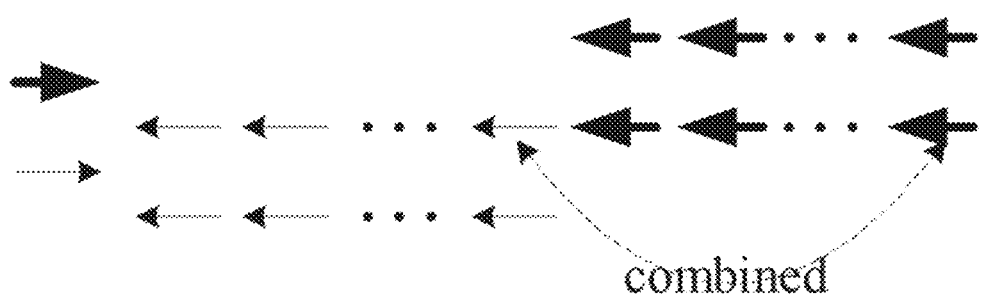
FIG. 2B is a schematic diagram showing the scanning mechanism of color blood flow imaging.
Figure 2A:
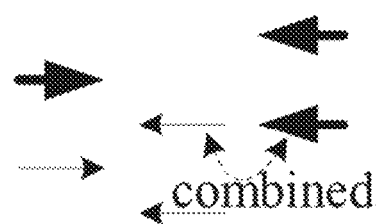
FIG. 2A is a schematic diagram showing the scanning mechanism of tissue imaging.

The transmission mechanism shown in FIG. 2(a) is that used for tissue imaging. Taking combining double received beams into one line as a simple example, a receiving line corresponding to a previous transmission at a receiving position is combined with another receiving line corresponding to a next transmission at the same receiving position; and in this respect, the time delay difference between such two receiving lines participating in the combination is exactly a pulse repeated time (PRT).

When combining beams, the movement of the target is required to be less than half wavelength within the delay difference between the combining lines, so that signal cancellation will not affect the signal-to-noise ratio during the combination. Of course, the velocity and displacement of the target motion can also be estimated by motion estimation, which can be compensated to the complex delay.

The transmission mechanism shown in FIG. 2(b) is that used for color blood flow imaging, which is also illustrated by combining double beams into one line. In color imaging, there needs to transmit 8 to 16 times at the same receiving line location, which is referred to as a scanning packet; that is, one transmitting line in FIG. 2(b) may represent a scanning packet, and 8 to 16 receiving lines referred to as packet size may be received for one scanning packet. When the receiving lines are combined subsequently, the receiving line transmitted for the first time in the last packet size may be combined with the receiving line transmitted for the first time in the next packet size, and so on. As shown in FIG. 2(b), "combining" may refer to combining a receiving line that is last transmitted in a first scanning packet with a receiving line that is last transmitted in a second scanning packet. Such that, the delay difference between the combining singles may be 8 to 16 times the PRT. However, the blood flow signal is moving per se with a relative fast velocity at the most, which does not meet the restriction that the movement of the target for the combined beam does not exceed half wavelength, leading to cancellation of echo signals due to phase change during the composition and reduction of the signal-to-noise ratio. More seriously, in the color blood flow imaging mode, there is also an alternate scanning mode for the transmission scanning mechanism; such that the delay difference among the combining lines may be longer, that is the number of alternation multiplying the number of scanning packets times the PRT.

Therefore, it is theoretically infeasible to apply the transmission continuous focusing methods for tissue imaging directly to the color blood flow imaging mode. New methods are needed to improve the lateral resolution of image(s) together with the sensitivity and penetration of image(s).

An ultrasonic imaging method, which can be applied to blood flow imaging and can improve the quality of color images, is provided in an embodiment of the present disclosure.

FIG. 3 schematically shows a flowchart of an ultrasonic imaging method according to an embodiment of the present disclosure. The method shown in FIG. 3 may include:

Step S101: transmitting an ultrasonic wave to a region of interest of a target object and receiving an ultrasonic echo based on the ultrasonic wave to obtain an ultrasonic echo signal;

Step S102: processing the ultrasonic echo signal to obtain an autocorrelation function characterizing a blood flow signal;

S103: performing complex coefficient weighting on the autocorrelation function characterizing a blood flow signal to obtain a synthetic autocorrelation function; and Step S104: obtaining a color blood flow image of the region of interest based on the synthetic autocorrelation function.

As an example, the region of interest in step S101 may include a blood flow region.

As an example, the process in step S102 may include beam synthesis and autocorrelation calculation. Specifically, step S102 may include: performing beam synthesis on the ultrasonic echo signal to obtain a beam synthesized signal; and processing the beam synthesized signal in autocorrelation domain to obtain the autocorrelation function representing a blood flow signal.

As an example, the autocorrelation function may include N, D and R. Specifically, the autocorrelation function may include a zero-order autocorrelation function R, a real part D of a first-order autocorrelation function, and an imaginary part N of the first-order autocorrelation function.

Correspondingly, the complex coefficient weighting in step S103 may include: for each receiving line, performing complex coefficient weighting on R, N, D respectively to obtain a synthetic R, a synthetic N and a synthetic D. The complex coefficient adopted during weighting may be a transmission continuous focusing synthesis coefficient.

Further, the ultrasonic wave in step S101 may be transmitted for multiple times, and the synthetic R, synthetic N and synthetic D obtained after each transmission may be accumulated respectively. Specifically, for each receiving line, accumulating the synthetic R, the synthetic N, the synthetic D obtained by multiple transmission respectively to obtain a cumulative synthetic R, a cumulative synthetic N and a cumulative synthetic D.

Correspondingly, it may be understood that for the multiple transmission, the synthetic autocorrelation function in step S104 may include: accumulating the synthetic R, accumulating the synthetic N and accumulating the synthetic D.

Figure 4:
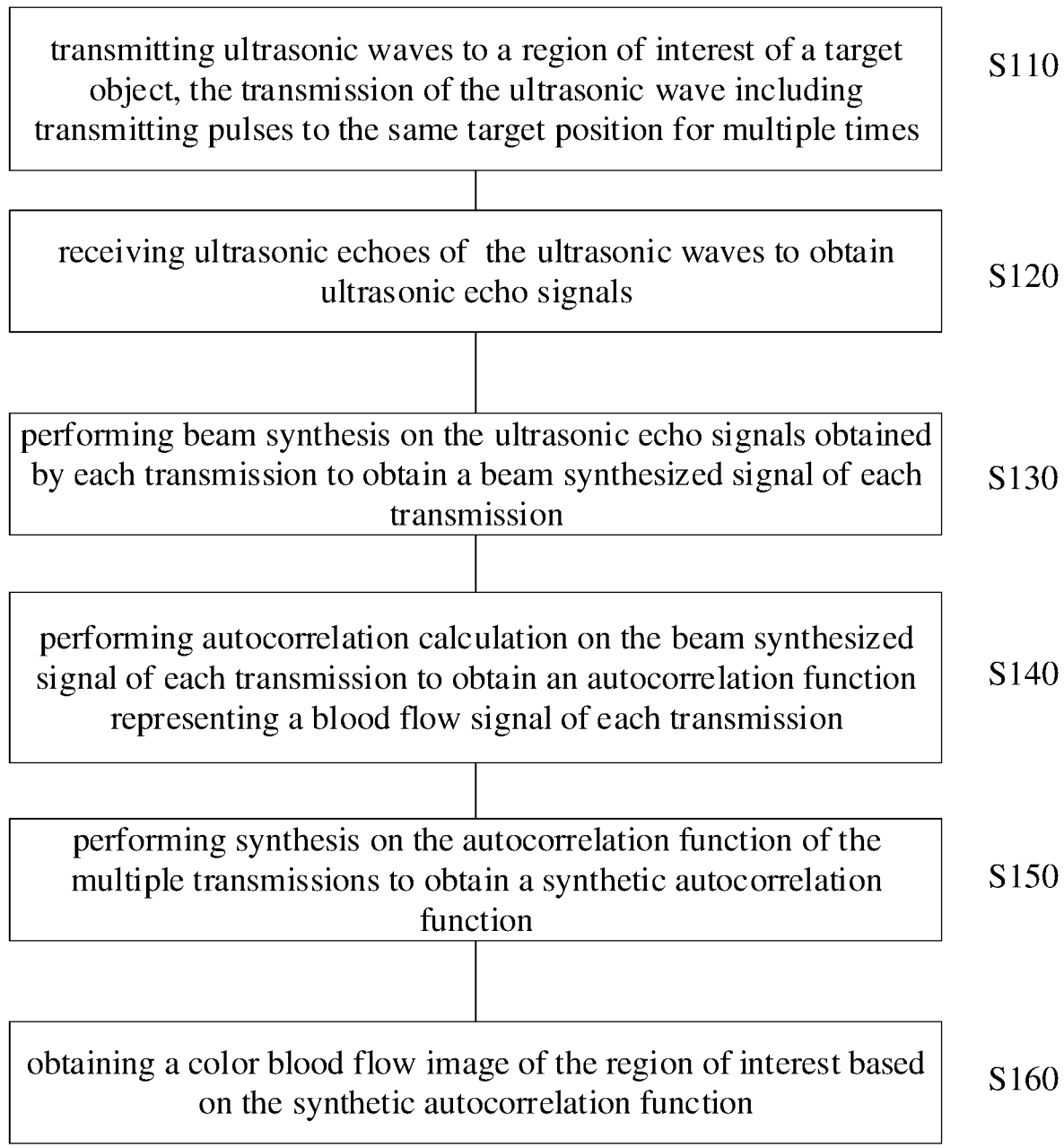
FIG. 4 is a schematic flowchart of an ultrasonic imaging method according to another embodiment of the present disclosure.

As an example, the ultrasonic wave in step S101 may be transmitted a plurality of times, and each transmission may include a plurality of pulses. As shown in FIG. 4, the ultrasonic imaging method may include:

Step S110: transmitting an ultrasonic wave to a region of interest of a target object, the transmission of the ultrasonic wave comprising transmitting pulses to the same target position for multiple times;

Step S120: receiving an ultrasonic echo based on the ultrasonic wave to obtain an ultrasonic echo signal;

Step S130: performing beam synthesis on the ultrasonic echo signal obtained by each transmission to obtain a beam synthesized signal of each transmission;

Step S140: performing autocorrelation calculation on the beam synthesized signal of each transmission to obtain an autocorrelation function characterizing a blood flow signal of each transmission;

Step S150: performing synthesis on the autocorrelation functions characterizing a blood flow signal obtained after multiple transmissions to obtain a synthetic autocorrelation function; and Step S160: obtaining a color blood flow image of the region of interest based on the synthetic autocorrelation function.

As an example, the region of interest in step S110 may include a blood flow region.

As an example, multiple transmissions may be made to the region of interest, such as two or more. Each transmission may include multiple pulses, such as any one of 8 to 16. Multiple pulses transmitted and received in one transmission can form a scanning packet. It may be understood that multiple (e.g. two) scanning packets may be formed by multiple (e.g. two) transmissions and receptions, each scanning packet including multiple (e.g. 8 or 16) pulses.

As an example, beam synthesis in step S130 can include: amplifying, analog-to-digital converting and demodulating to baseband the ultrasonic echo signal through each channel to obtain a baseband signal.

As an example, step S140 may include: obtaining the autocorrelation function by first wall filtering the baseband signal (IQ) outputted in step S130 and then performing autocorrelation calculation.

That is, before the autocorrelation calculation, it may include the following processes: amplification, analog-to-digital conversion (DAC), beam synthesis, digital demodulation, and wall filtering. In other words, it may be understood that the processing in step S130 may include: signal amplification, analog-to-digital conversion, digital demodulation, and beam synthesis. The processing in step S140 may include: wall filtering, and autocorrelation calculation.

Figure 5:
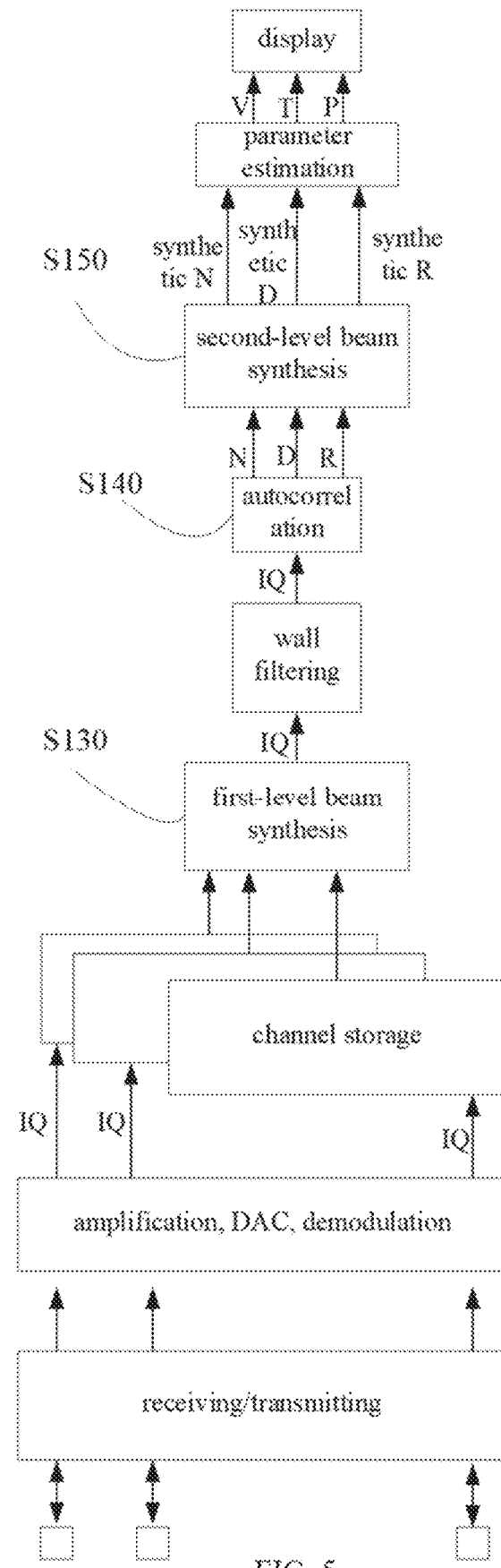
FIG. 5 is a schematic flowchart of ultrasonic color blood flow imaging according to an embodiment of the present disclosure.

As another example, with reference to FIG. 5, before step S130, the ultrasonic echo signal may be amplified, analog-to-digital converted and demodulated to baseband through each channel, and then stored in a channel register. Further, beam synthesis may be carried out in step S130 to obtain the beam-synthesized signal.

In an embodiment, analog-to-digital conversion is used to convert analog signals to digital signals. Digital demodulation may demodulate signals into an orthogonal complex signal, including an in-phase component I and an orthogonal component Q.

In an embodiment, wall filtering, which may be for example implemented by a high-pass filter, may be used to filter stationary and slow-moving tissue signals, such as signals of blood vessel walls, valves, stationary tissues, etc.

In an embodiment, autocorrelation calculation may include delayed autocorrelation processing, for example, including at least one of an addition circuit, subtraction circuit, multiplication circuit, integration circuit, average operation circuit, etc.

In an embodiment, the autocorrelation function may include a zero-order autocorrelation function (R), a real part of a first-order autocorrelation function (D), and an imaginary part of the first-order autocorrelation function (N). R may represent the energy of blood flow, a complex number composed of N and D (i.e. the first-order autocorrelation function) may be used to determine the angular frequency of the movement of blood flow.

It can be seen that the autocorrelation function obtained in step S102 or S140 no longer has a time series characterizing the Doppler frequency shift of signals. For example, R in the autocorrelation function is only the energy of blood flow without phase information. N and D are used to represent a complex number, but the complex number is a scalar. Therefore, subsequent composite processing based on the autocorrelation function may be based on scalar processing, avoiding the possibility of energy offset due to opposite phases of signals.

Thus, for each transmission, an autocorrelation function can be derived in accordance with the method of steps S110 to S140. For multiple transmissions, autocorrelation functions for the corresponding multiple transmissions may be obtained. Exemplarily, in step S150, the autocorrelation functions representing blood flow signals for the multiple transmissions may be weighted and synthesized to obtain a synthesized autocorrelation function.

In an embodiment, a synthesis coefficient for being weighted and synthesized may be expressed as f, which may satisfy: $\tilde{f}=(B^H B)^{-1} B^H \bar{d}$, where $\tilde{f}$ is the inverse of f, B is a convolution operator representing $R(\theta)T(\theta)$ in vector form, $R(\theta)T(\theta)$ represents a receiving-transmitting pattern, $\bar{d}$ represents a vector of an expected beam pattern, and H represents conjugate transpose. $T(\theta)$ may be determined depend on transmitting aperture, transmitting frequency, transmitting focus and transmitting interval; and $R(\theta)$ may be determined depend on receiving aperture and receiving line interval. The synthesis coefficient will be described in more detailed below with reference to FIG. 7.

In fact, there may be considered to have two-level synthesis in the method according to embodiments of the present disclosure, namely, a first-level synthesis being the beam synthesis in step S130 and a second-level synthesis being the synthesis in step S150, respectively. The first-level synthesis is located in a beam synthesis step, and the second-level synthesis is located in the signal processing step. Specifically, the second-level synthesis is located after the autocorrelation calculation; and the autocorrelation functions in the autocorrelation domain, which no longer have the time series characterizing the Doppler shift of signals, are all scalars, so the second-level synthesis may be processed as scalars.

It can be understood that the second-level synthesis is carried out for information about the multiple transmissions, i.e., the transmission continuous focusing method(s) may be embodied in the second-level synthesis. That is to say, with regard to the color blood flow mode in the embodiments of the present disclosure, the transmission continuous focusing method(s) may be performed in the autocorrelation domain. Actually, from the perspective of information theory, the implementation of the transmission continuous focusing method(s) also describes the expression of reflected signals of a scanned object under the same transmitting acoustic waves; and with regard to a single transmission of color blood flow imaging (which may include multiple pulses forming a packet size of a scanning packet), a frame of information including the number of points and the number of receiving lines may also outputted in the autocorrelation domain.

In another embodiment, the synthesis in step S150 may include: based on a relative delay difference of different transmissions, selecting a corresponding autocorrelation storage data for accumulation. It may be understood that this is a quasi-synthetic arithmetic structure which adopts the delay difference of different transmission for delay addition.

In yet another embodiment, the synthesis in step S150 may include: obtaining the synthetic autocorrelation function of each receiving line by complex coefficient weighting of the autocorrelation functions on each receiving line along the number of receiving lines and summation of the autocorrelation functions of multiple transmission by an accumulator. The synthetic autocorrelation function may include the synthetic R, the synthetic D and the synthetic N.

It should be noted that the receiving line (also referred to as a receiving scan line) may be actually no longer a necessary concept for an ultrasonic device using transmission continuous focusing method(s); and with regard to any point in the scanning space, it may be regarded as a composite accumulation of echoes from all transmissions at this point, which may also be referred to as point-by-point focusing. In a practical scenario, the concept of the receiving line is still employed primarily for ease of storage, processing and description. It will be appreciated that the weighted and synthesized along the receive line(s) described in step S150 in the embodiment does not necessarily imply the existence of a receiving line.

Further, in step S160, the velocity (V), energy (P) and variance (T) of blood flow can be calculated by parameter estimation based on synthetic autocorrelation functions (such as the synthetic R, the synthetic D and the synthetic N), and a color blood flow image can be obtained and presented on the display 150 after steps including DSC (digital scan conversion) and post-processing. Illustratively, the embodiment shown in FIG. 4 may also be represented as a schematic flowchart as shown in FIG. 5 or FIG. 6.

Figure 6:
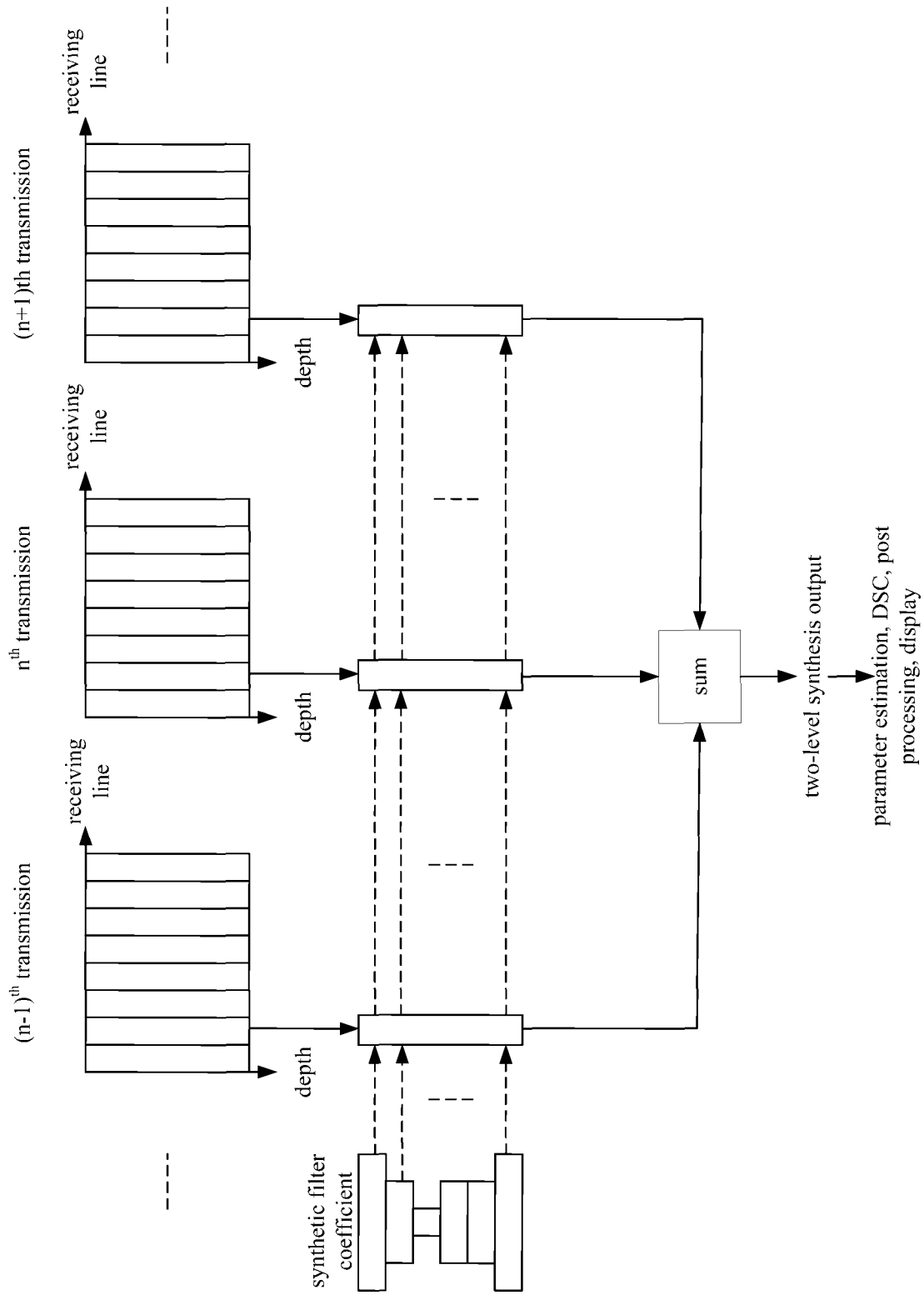
FIG. 6 is a schematic flowchart of ultrasonic color blood flow imaging according to another embodiment of the present disclosure.

Specifically, assume that the $n^{th}$ transmission in FIG. 6 is the current transmission, the $(n-1)^{th}$ transmission is the last transmission, and the $(n+1)^{th}$ transmission is the next transmission. The ultrasonic waves transmitted each time (referred to as a packet of transmissions, or packet size) generates an autocorrelation function for a frame, where the number of points of a frame is equal to the number of points per receiving line multiplying the number of receiving lines. The autocorrelation function corresponding to the number of frames can be generated based on the completion of scanning a frame with color transmission of the number of packet size. The N, D and R of each frame are stored separately, and are synthesized separately when performing transmission continuous focusing method(s). In other words, the N, D and R on a certain receiving line along the direction of the receiving line are weighted by complex coefficients respectively, and then they are accumulated by an accumulator (summation in FIG. 6), which is the output of the second-level synthesis of the certain receiving line, namely, the synthesis N, the synthesis D and the synthesis R. After that, i.e. on the basis of the two-level synthetic output in FIG. 6, parameters estimation, DSC, post-processing and other steps may also be carried out, and display may then be performed by the display.

It can be seen therefrom that, with the method(s) in the embodiments of the present disclosure, a synthesis process based on transmission continuous focusing can be implemented in an autocorrelation domain; specifically, synthesis is performed after obtaining an autocorrelation function by autocorrelation calculation, and it can be processed only based on scalar(s), thus avoiding energy offset due to opposite phases of signals caused by blood flow characteristics, improving the lateral resolution of a color blood flow image and enhancing the sensitivity and penetration of the blood flow image.

Exemplarily, the second-level synthesis can be accomplished by the summation of weighted complex coefficients in an embodiment of the present disclosure, where a complex coefficient may be referred to as a continuous-transmit-focusing synthesis coefficient. It will be appreciated that before performing the second-level synthesis, the complex coefficients need to be determined and then synthesized.

The complex coefficient(s), the continuous-transmit-focusing synthesis coefficient(s) may actually be equivalent to filter coefficient(s) in an embodiment of the present disclosure. The reason is that, a traditional imaging method for tissue imaging or color blood flow imaging is generally transmitting with single-point focusing and receiving with dynamic focusing. Such a transmitting/receiving focus mode may result in an image at a transmitting focus with a best lateral resolution and a highest signal-to-noise ratio. Because the energy is most concentrated at the transmitting focus, and the main lobe of the pattern of a transmitted beam is narrowest. The goal of the transmission continuous focusing method(s) is to optimize a transmitting-receiving two-way pattern at a non-transmitting focus close to a transmitting-receiving two-way pattern at the transmitting focus. This is equivalent to generating an equivalent transmitting focus at the non-transmitting focus, which may be technically a problem of an optimal filtering, wherein an input of the optimal filter may be a transmitting-receiving pattern at a non-transmitting focus and an expected output of the optimal filter may be a transmitting-receiving pattern at the transmitting focus.

Correspondingly, an ultrasonic signal processing method provided in accordance with an embodiment of the present disclosure may, as shown in FIG. 7, include:

Step S210: transmitting an ultrasonic wave to a region of interest of a target object and receiving an ultrasonic echo based on the ultrasonic wave to obtain an ultrasonic echo signal;

Step S220: performing beam synthesis on the ultrasonic echo signal to obtain a beam synthesized signal;

Step S230: processing the beam synthesized signal in autocorrelation domain to obtain an autocorrelation function representing a blood flow signal; and Step S240: processing the autocorrelation function representing a blood flow signal with an operation structure of an optimal filter.

Step S220 may be implemented with reference to the description of step S130. For example, the beam synthesis in step S220 may be the first-level synthesis, and before the beam synthesis, it may also include: amplification, analog-to-digital conversion, demodulation and other processing.

Step S230 may be implemented with reference to the description of step S140. For example, there may include wall filtering before the autocorrelation calculation in step S230, and for another example the autocorrelation function in step S230 may include N, D and R.

In an example, step S240 may include: using an operation structure of an optimal filter to determine the optimal filter coefficient, based on which weighting and summing may be performed on the autocorrelation function of multiple transmissions.

In an embodiment, the optimal filter may minimize a squared error between a filtered beam pattern and an expected beam pattern, i.e., the optimal filter may be a filter that minimizes a squared error between a filtered beam pattern and an expected beam pattern.

In an implementation, the optimal filter coefficient may be obtained based on minimum mean square error.

Assuming that the filter coefficient of the optimal filter (short for the optimal filter coefficient or filter coefficient) is represented by f, the optimal filter coefficient f may meet:

$$\tilde{f}=(B^H B)^{-1} B^H \bar{d},$$

where $\tilde{f}$ is the inverse of f, B is a convolution operator representing $R(\theta)T(\theta)$ in vector form, $R(\theta)T(\theta)$ represents a receiving-transmitting pattern; $\bar{d}$ represents a vector of an expected beam pattern, and H represents conjugate transpose. $T(\theta)$ may be determined depend on transmitting aperture, transmitting frequency, transmitting focus, transmitting interval; and $R(\theta)$ may be determined depend on receiving aperture, receiving line interval.

As an alternative implementation, the optimal filter coefficient may be determined by the following means. The optimal filter coefficient, which is a complex coefficient, may include a weighted amplitude and a weighted phase. For example, the delay difference of any point in the scanning space to the center of the transmitting aperture may be taken as a weighted phase. Different intensities of acoustic field corresponding to transmissions to the point may be taken as a weighted amplitude.

For example, step S240 may include: obtaining the autocorrelation function by performing weighting and summation; further it may also include: obtaining a color blood flow image after parameter estimation, DSC, post processing and so on for being displayed on the display. The synthetic autocorrelation function may include the synthesis N, the synthesis D and the synthesis R.

In addition, it should be noted that the determination of complex coefficients in step S103, step S150, or step S240 in embodiments of the present disclosure (also referred to as continuous-transmit-focusing synthesis coefficients, optimal filter coefficients, or filter coefficients) may be achieved using hardware and/or software. Specifically, it may employ hardware such as a field programmable gate array (FPGA) for implementation; or it may also be implemented using software, such as a central processing unit (CPU) and a graphics processing unit (GPU); or it may use a combination of software and hardware for implementation. The present disclosure is not limited to this.

Now return to the ultrasonic imaging system 10 shown in FIG. 1.

In one implementation, the transmitting circuit 160 may send an excitation pulse to the ultrasonic probe 110 via the transmitting/receiving selection switch 120 to excite the ultrasonic probe 110 to transmit an ultrasonic beam to the region of interest of the target object, which may include blood vessels. The receiving circuit 170 may receive the ultrasonic echo of the returned ultrasonic beam through the ultrasonic probe 110 to obtain the ultrasonic echo signal which is sent to the processor 140. The transmitted ultrasonic wave may include sending multiple pulses to the same target location. The processor 140 may carry out beam synthesis for ultrasonic echo signal obtained by each transmission to obtain the beam-synthesized signal of each transmission. The autocorrelation function characterizing blood flow signals may be obtained by calculating the beam-synthesized signals of each transmitted beam. The autocorrelation function characterizing blood flow signals may be synthesized to obtain the synthesized autocorrelation function. The color blood flow image of the region of interest may be obtained based on the synthetic autocorrelation function. The monitor 150 may display the color blood flow image.

Furthermore, a computer storage medium also provided in an embodiment may store a computer program. When the computer program is executed by a computer or processor, the steps of the methods shown in any of FIG. 3 to FIG. 7 above can be implemented. For example, the computer storage medium is the computer readable storage medium.

In one embodiment, the computer program instruction may cause the computer or processor to perform the following steps while being run by the computer or processor: transmitting an ultrasonic wave to a region of interest of a target object, said transmitting an ultrasonic wave comprising transmitting pulses to a same target position for multiple times; receiving an ultrasonic echo based on the ultrasonic wave to obtain an ultrasonic echo signal; performing beam synthesis on the ultrasonic echo signal obtained by each transmission to obtain a beam-synthesized signal of each transmission; performing autocorrelation calculation on the beam-synthesized signal of each transmission to obtain an autocorrelation function representing a blood flow signal of each transmission; performing synthesis on the autocorrelation function representing a blood flow signal obtained by multiple transmission to obtain a synthetic autocorrelation function; and obtaining a color blood flow image of the region of interest based on the synthetic autocorrelation function.

In one embodiment, the computer program instruction may cause the computer or processor to perform the following steps while being run by the computer or processor: transmitting an ultrasonic wave to a region of interest of a target object and receiving an ultrasonic echo based on the ultrasonic wave to obtain an ultrasonic echo signal; processing the ultrasonic echo signal to obtain an autocorrelation function representing a blood flow signal; performing complex coefficient weighting on the autocorrelation function representing a blood flow signal to obtain a synthetic autocorrelation function; and obtaining a color blood flow image of the region of interest based on the synthetic autocorrelation function.

In one embodiment, the computer program instruction may cause the computer or processor to perform the following steps while being run by the computer or processor: transmitting an ultrasonic wave to a region of interest of a target object and receiving an ultrasonic echo based on the ultrasonic wave to obtain an ultrasonic echo signal; performing beam synthesis on the ultrasonic echo signal to obtain a beam-synthesized signal; processing the beam synthesized signal in autocorrelation domain to obtain an autocorrelation function representing a blood flow signal; and processing the autocorrelation function representing a blood flow signal with an operation structure of an optimal filter.

The computer storage medium may include, for example, a memory card for a smart phone, a memory component for a tablet computer, a hard disk for a personal computer, a read-only memory (ROM), an erasable programmable read-only memory (EPROM), a portable compact disk read-only memory (CD-ROM), a USB memory, or any combination of the above. The computer readable storage medium may be any combination of one or more computer readable storage media.

In addition, a computer program product or a computer program device containing instructions which, when executed by a computer, may cause the computer to perform the steps of the method shown in any one of FIG. 3 to FIG. 7 above is provided in an embodiment of the present disclosure.

It can be seen therefrom that, with the embodiments of the present disclosure, a synthesis process based on transmission continuous focusing can be implemented in an autocorrelation domain; specifically, synthesis is performed after obtaining an autocorrelation function by autocorrelation calculation, and it can be processed only based on scalar(s), thus avoiding energy offset due to opposite phases of signals caused by blood flow characteristics, improving the lateral resolution of a color blood flow image and enhancing the sensitivity and penetration of the blood flow image.

While exemplary embodiments have been described herein with reference to the accompanying drawings, it should be understood that the above example embodiments are merely illustrative and are not intended to limit the scope of the disclosure thereto. Those skilled in the art may make various changes and modifications therein without departing from the scope and spirit of the disclosure. All such changes and modifications are intended to be included in the scope of the disclosure as claimed in the appended claims.

A person of ordinary skill in the art may be aware that, in combination with the examples described in the embodiments disclosed in this specification, units and algorithm steps may be implemented by using electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the present disclosure, it should be understood that the disclosed devices and methods may be implemented in other ways. For example, the device embodiments described above are merely exemplary. For example, the division of units is merely a logical function division. In actual implementations, there may be other division methods. For example, a plurality of units or components may be combined or integrated into another device, or some features may be omitted or not implemented.

A large number of specific details are explained in this specification provided herein. However, it can be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention, namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, wherein each claim itself serves as an individual embodiment of the disclosure.

Those skilled in the art should understand that, in addition to the case where features are mutually exclusive, any combination may be used to combine all the features disclosed in this specification (along with the appended claims, abstract, and drawings) and all the processes or units of any of methods or devices as disclosed. Unless explicitly stated otherwise, each feature disclosed in this specification (along with the appended claims, abstract, and drawings) may be replaced by an alternative feature that provides the same, equivalent, or similar object.

Furthermore, those skilled in the art should understand that although some of the embodiments described herein comprise some but not other features included in other embodiments, combinations of features of different embodiments are meant to be within the scope of the disclosure, and form different embodiments. For example, in the claims, any one of the embodiments set forth thereby can be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules according to the embodiments of the disclosure. The disclosure may further be implemented as an apparatus program (e.g. a computer program and a computer program product) for executing some or all of the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The word "comprising" does not exclude the presence of elements or steps not listed in a claim. The word "a" or "an" preceding an element does not exclude the presence of a plurality of such elements. The disclosure may be implemented by means of hardware comprising several different elements and by means of an appropriately programmed computer. In unit claims listing several ultrasound devices, several of these devices may be specifically embodied by one and the same item of hardware. The use of the terms "first", "second", "third", etc. does not indicate any order. These terms may be interpreted as names.

The above is only the specific embodiment of the present disclosure or the description of the specific embodiment, and the protection scope of the present disclosure is not limited thereto. Any changes or substitutions should be included within the protection scope of the present disclosure. The protection scope of the present disclosure shall be subject to the protection scope of the claims.

The invention claimed is:

1. An ultrasonic imaging method, comprising:
   transmitting ultrasonic waves to a region of interest of a target object, said transmitting ultrasonic waves comprising transmitting pulses to a same target position for multiple times;
   receiving ultrasonic echoes of the ultrasonic waves to obtain ultrasonic echo signals;
   performing a beam synthesis on the ultrasonic echo signals obtained by each transmission to obtain a beam synthesized signal of each transmission;
   performing an autocorrelation calculation on the beam synthesized signal of each transmission to obtain an autocorrelation function of each transmission representing a blood flow signal;
   performing a synthesis on the autocorrelation functions of the multiple transmissions to obtain a synthetic autocorrelation function; and
   obtaining a color blood flow image of the region of interest according to the synthetic autocorrelation function.

2. The method according to claim 1, wherein the beam synthesized signal of each transmission is a frame of beam synthesized signal comprising multiple receiving lines, wherein each receiving line comprising multiple points.

3. The method according to claim 2, wherein said performing a synthesis on the autocorrelation functions of the multiple transmissions to obtain a synthetic autocorrelation function comprises:
   performing a complex coefficient weighting on the autocorrelation functions on each receiving line and summing the weighted autocorrelation functions of multiple transmission by an accumulator to obtain the synthetic autocorrelation function of each receiving line.

4. The method according to claim 1, wherein said performing a synthesis on the autocorrelation functions of the multiple transmissions to obtain a synthetic autocorrelation function comprises:
   performing a weighted synthesis on the autocorrelation functions of the multiple transmissions to obtain the synthetic autocorrelation function.

5. The method according to claim 4, wherein a synthesis coefficient f of the weighted synthesis meets: $\bar{f}=(B^H B)^{-1} B_H \bar{d}$,
   where $\bar{f}$ is the inverse of f, B is a convolution operator representing $R(\theta)T(\theta)$ in vector form, $R(\theta)T(\theta)$ represents a receiving-transmitting pattern; $\bar{d}$ represents a vector of an expected beam pattern, and H represents conjugate transpose.

6. The method according to claim 5, wherein
   $T(\theta)$ is determined depend on a transmitting aperture, a transmitting frequency, a transmitting focus and a transmitting interval; and
   $R(\theta)$ is determined depend on a receiving aperture and a receiving line interval.

7. The method according to claim 1, wherein the autocorrelation function comprises a zero-order autocorrelation function R, a real part D of a first-order autocorrelation function, and an imaginary part N of the first-order autocorrelation function.

8. The method according to claim 7, wherein performing a synthesis on the autocorrelation functions of the multiple transmissions to obtain a synthetic autocorrelation function comprises:
performing a synthesis on the zero-order autocorrelation function R, the real part D of the first-order autocorrelation function, and the imaginary part N of the first-order autocorrelation function respectively to obtain a synthetic R, a synthetic D and a synthetic N.

9. The method according to claim 1, before the autocorrelation calculation, further comprising an amplification, an analog-to-digital conversion, a digital demodulation or a wall filtering.

10. The method according to claim 1, wherein the transmitting and receiving of the pulses for multiple times form a scanning packet, a packet size thereof being any one of 8 to 16 times.

11. An ultrasonic imaging method, comprising:
transmitting an ultrasonic wave to a region of interest of a target object and receiving an ultrasonic echo of the ultrasonic wave to obtain an ultrasonic echo signal;
processing the ultrasonic echo signal to obtain an autocorrelation function representing a blood flow signal;
performing a complex coefficient weighting on the autocorrelation function to obtain a synthetic autocorrelation function; and
obtaining a color blood flow image of the region of interest based on the synthetic autocorrelation function.

12. The method according to claim 11, wherein processing the ultrasonic echo signal to obtain an autocorrelation function representing a blood flow signal comprises:
performing a beam synthesis on the ultrasonic echo signal to obtain a beam synthesized signal; and
processing the beam synthesized signal in autocorrelation domain to obtain the autocorrelation function.

13. The method according to claim 11, wherein a complex coefficient of the complex coefficient weighting is a transmission continuous focusing synthesis coefficient.

14. The method according to claim 11, wherein, the autocorrelation function comprises a zero-order autocorrelation function R, a real part D of a first-order autocorrelation function, and an imaginary part N of the first-order autocorrelation function; and performing a complex coefficient weighting on the autocorrelation function to obtain a synthetic autocorrelation function comprises:
for each receiving line, performing a complex coefficient weighting on R, N, D respectively to obtain a synthetic R, a synthetic N and a synthetic D.

15. The method according to claim 14, wherein the ultrasonic wave is transmitted for multiple times, and the method further comprises:
for each receiving line, accumulating the synthetic R, the synthetic N, the synthetic D obtained by the multiple transmissions respectively to obtain a cumulative synthetic R, a cumulative synthetic N and a cumulative synthetic D.

16. An ultrasonic signal processing method, comprising:
transmitting an ultrasonic wave to a region of interest of a target object and receiving an ultrasonic echo of the ultrasonic wave to obtain an ultrasonic echo signal;
performing a beam synthesis on the ultrasonic echo signal to obtain a beam synthesized signal;
processing the beam synthesized signal in autocorrelation domain to obtain an autocorrelation function representing a blood flow signal; and
processing the autocorrelation function with an operation structure of an optimal filter.

17. The method according to claim 16, wherein the optimal filter is a filter that minimizes a squared error between a filtered beam pattern and an expected beam pattern.

18. The method according to claim 16, wherein a filter coefficient of the optimal filter meets:

$$\tilde{f}=(B^H B)^{-1} B^H \vec{d},$$

where $\tilde{f}$ is the inverse of f, B is a convolution operator representing $R(\theta)T(\theta)$ in vector form, $R(\theta)T(\theta)$ represents a receiving-transmitting pattern; $\vec{d}$ represents a vector of an expected beam pattern, and H represents conjugate transpose.

19. The method according to claim 18, wherein
$T(\theta)$ is determined depend on a transmitting aperture, a transmitting frequency, a transmitting focus and a transmitting interval; and
$R(\theta)$ is determined depend on a receiving aperture and a receiving line interval.

* * * * *

UNITED STATES PATENT AND TRADEMARK OFFICE
CERTIFICATE OF CORRECTION

PATENT NO. : 12,239,480 B2  
APPLICATION NO. : 18/082263  
DATED : March 4, 2025  
INVENTOR(S) : Dong et al.

Page 1 of 1

It is certified that error appears in the above-identified patent and that said Letters Patent is hereby corrected as shown below:

In the Claims

In Claim 5 Column 14 Line 50, "coefficient f of the weighted synthesis meets: $\bar{f}=(B^H B)^{-1} B_H \bar{d}$," should read -- coefficient f of the weighted synthesis meets: $\bar{f}=(B^H B)^{-1} B^H \bar{d}$, --

Signed and Sealed this  
Third Day of June, 2025

Coke Morgan Stewart  
*Acting Director of the United States Patent and Trademark Office*